United States Patent
Seeger et al.

(10) Patent No.: US 11,007,155 B2
(45) Date of Patent: May 18, 2021

(54) METHOD FOR PRODUCING A SEA URCHIN EXTRACT ENRICHED WITH 1,4-POLYHYDROXYLATED NAPHTHOQUINONES WITH ANTIMICROBIAL AND ANTIOXIDANT ACTIVITY

(71) Applicants: Universidad Técnica Federico Santa María, Valparaíso (CL); Knop Laboratorios S.A., Quilpué (CL)

(72) Inventors: Michael Seeger, Valparaíso (CL); Erwin Strahsburger, Valparaíso (CL); Myriam González, Valparaíso (CL); Franco Cárdenas, Valparaíso (CL)

(73) Assignees: Universidad Técnica Federico Santa María, Valparaíso (CL); Knop Laboratorios S.A., Quilpué (CL)

( * ) Notice: Subject to any disclaimer, the term of this patent is extended or adjusted under 35 U.S.C. 154(b) by 198 days.

(21) Appl. No.: 16/349,406

(22) PCT Filed: Nov. 14, 2017

(86) PCT No.: PCT/CL2017/050064
§ 371 (c)(1),
(2) Date: May 13, 2019

(87) PCT Pub. No.: WO2018/085955
PCT Pub. Date: May 17, 2018

(65) Prior Publication Data
US 2019/0365670 A1    Dec. 5, 2019

(30) Foreign Application Priority Data

Nov. 14, 2016    (CL) .................................. 2895-2016

(51) Int. Cl.
*A61K 36/00*    (2006.01)
*A61K 31/122*    (2006.01)

(52) U.S. Cl.
CPC .................................. *A61K 31/122* (2013.01)

(58) Field of Classification Search
CPC ....................................................... A61K 36/00
USPC ......................................................... 424/725
See application file for complete search history.

(56) References Cited

PUBLICATIONS

Griffiths, M. A study of the synthesis of naphthaquinone pigments by the larvae of two species of sea urchins and their reciprocal hybrids. Developmental biology, 1965, vol. 11, No. 3, p. 433-447.

Abubakar, L. et al. Antimicrobial activity of various extracts of the sea urchin Tripneustes gratilla (Echinoidea). African Journal of Pharmacology and Therapeutics, 2012, vol. 1, No. 1.[on line], [retrieved on Jan. 9, 2016].

Canales, D. H. et al. El "erizo de mar" Tetrapygus niger como marcador biol6gico de estres oxidativo. Revista Peruana de Biologia, 2000, vol. 7, No. 2, p. 198-201.

Hamaguchi, Y. et al., Activation of sea urchin eggs by microinjection of calcium buffers. Experimental cell research, 1981, vol. 134, No. 1, p. 171-179.

Perry, G., et al., "Ca2+-stimulated production of H2O2 from naphthoquinone oxidation in Arbacia eggs," Experimental cell research, 1981, vol. 134, No. 1, p. 65-72. DOI: 10.1016/0014-4827(81)90463-8.

Firon, N., et al., "Isolation and properties of a soluble fraction of Paracentrotus lividus sea urchin eggs responsible for the calcium-induced oxidative burst," Experimental cell research, 1990, vol. 188, No. 1, p. 10-15.

Fabbrocinbi, A., et al., "Histological Examination of the Gonads of Paracentrotus LIvidus (LMK, 1816) from the Southern Adriatic Coast," Biol. Mar. Mediterr., vol. 17(1): pp. 272-273 (2010).

Fuentes, I., et al., "Larval Development and Metamorphosis of Cultured Tetrapygus Niger (Echinodermata Echinoidea): an Uncommon Form of Echinoplutei," Invertebrate Reproduction and Development, vol. 37(3): pp. 201-209 (2000).

Ho, E., et al., "Perturbation of Gut Bacteria induces a Coordinated Cellular Immune Response in the Purple Sea Urchin Lava." Immunology and Cell Biology. vol. 94, pp. 881-874 (2016).

*Primary Examiner* — Michael V Meller
(74) *Attorney, Agent, or Firm* — Elmore Patent Law Group, P.C.; Joseph Zucchero; Carolyn Elmore

(57) ABSTRACT

The invention refers to a method for obtaining polyhydroxy 1,4-naphthoquinones from live sea urchins, comprising the following steps:

a) injecting a KCl saline solution into the perivisceral coeloma of female sea urchins to induce spawning;

b) collecting the eggs, and grinding them into a fine powder;

c) mixing said fine powder with an alcoholic solvent;

d) separating the alcohol supernatant comprising the polyhydroxy 1,4-naphthoquinones in solution.

Where the polyhydroxy 1,4-naphthoquinones are selected from: echinochrome A (6-ethyl-2,3,5,7,8-pentahydroxy-1,4-naphthoquinone), spinochrome A (2-acetyl-3,5,6,8-tetrahydroxy-1,4-naphthoquinone), spinochrome B (2,3,5,7-tetrahydroxy-1,4-naphthoquinone), spinochrome C (2-acetyl-3,5,6,7,8-pentahydroxy-1,4-naphthoquinone), spinochrome D (2,3,5,6,8-pentahydroxy-1,4-naphthoquinone), spinochrome E (hexahydroxy-1,4-naphthoquinone) or mixtures thereof.

5 Claims, 2 Drawing Sheets

METHOD FOR PRODUCING A SEA URCHIN EXTRACT ENRICHED WITH 1,4-POLYHYDROXYLATED NAPHTHOQUINONES WITH ANTIMICROBIAL AND ANTIOXIDANT ACTIVITY

TECHNICAL FIELD

The invention consists of a method for obtaining, from living sea urchins, an extract enriched in polyhydroxylated 1,4-naphthoquinone pigments, especially in 6-ethyl-2,3,5,7, 8-pentahydroxy-1,4-naphthoquinone (echinochrome A, EqA), and also spinochrome A (2-acetyl-3,5,6,8-tetrahydroxy-1,4-naphthoquinone), spinochrome B (2,3,5,7-tetrahydroxy-1,4-naphthoquinone), spinochrome C (2-acetyl-3, 5,6,7,8-pentahydroxy-1,4-naphthoquinone), spinochrome D (2,3,5,6,8-pentahydroxy-1,4-naphthoquinone), spinochrome E (hexahydroxy-1,4-naphthoquinone) or mixtures thereof. The method comprises chemically inducing the spawning of female sea urchins and extracting the polyhydroxylated 1,4-naphthoquinones from the eggs, preserving the life of the sea urchin. In this extraction process, no acids or bases are used, but only organic solvents of low environmental impact such as ethanol and methanol. The product possesses antimicrobial activities against a wide range of pathogenic bacteria, including strains multiresistant to antibiotics, so it has applications to prevent or treat bacterial infections. In addition, the polyhydroxylated 1,4-naphthoquinones possess a high antioxidant activity.

BACKGROUND OF THE INVENTION

Spinochromes and echinochromes are polyhydroxylated 1,4-naphthoquinones and correspond to natural pigments found in sea urchins, especially in their spines and shells. These pigments provide the black, green or red color to these echinoderms. Additionally, these compounds are also present in other cells of sea urchins, probably with an active antimicrobial and antioxidant role.

The main spinochromes, due to their abundance and usefulness, are: spinochrome A (2-acetyl-3,5,6,8-tetrahydroxy-1,4-naphthoquinone), spinochrome B (2,3,5,7-tetrahydroxy-1,4-naphthoquinone), spinochrome C (2-acetyl-3, 5,6,7,8-pentahydroxy-1,4-naphthoquinone), spinochrome D (2,3,5,6,8-pentahydroxy-1,4-naphthoquinone) and spinochrome E (hexahydroxy-1,4-naphthoquinone). Its distribution varies in the different species of sea urchins. In the sea urchins *Echinus esculentus, Echinus elegans, Paracentrotus lividus* and *Strongylocentrotus franciscanus*, spinochromes A, B, C and E have been identified. Spinochromes A, B and D have been identified in the species *Pseudocentrotus depressus*. The species *Hemicentrotus mammillatus* possesses the Spinochromes A, B and C, while *Strongylocentrotus drobachiensis* possesses Spinochromes A, C, D and E (Anderson et al., Comp Biochem Physiol (1969), 28:333-.345).

On the other hand, in the sea urchins of the species *Echinus esculentus, Echinus elegans, Echinus esculentus, Strongylocentrotus franciscanus, Strongylocentrotus purpuratus, Strongylocentrotus droebachiensis* and *Paracentrotus lividus*, the equinochrome A (EqA), which corresponds to 6-ethyl-2,3,5,7,8-pentahydroxy-1,4-naphthoquinone, is found. This equinochrome is present in the urchin's coelomic fluid, in a concentration range of 30 to 60 □g/mL. It has been described that EqA accumulates within granules in the cytoplasm of the celomic cells, which are called red spherules. As part of the innate immune response of these echinoderms, in response to the presence of foreign particles, the red spherules secrete EqA into the coelomic fluid.

It is known in the state of the art that the polyhydroxylated 1,4-naphthoquinone molecules, besides being pigments, have antibiotic and antioxidant properties. It has been reported that methanol extracts enriched in polyhydroxy 1,4-naphthoquinones obtained from the shell of the purple urchin *Salmacis virgulata*, show a minimum inhibitory concentration (MIC) of 500 µg/ml for *Salmonella typhi* and *Vibrio chorelae* bacteria and a CMI of 125 µg/ml for *Proteus vulgaris* and *P. mirabilis*. This extract enriched in polyhydroxylated 1,4-naphthoquinones also possesses a high antioxidant activity, as explained later in the examples. The extract obtained by the method of the invention reaches an $EC_{50}$ of 18 µM, according to the DPPH test (a method to evaluate the oxidant activity). As a reference, the antioxidant activity of ascorbic acid in this same assay is an $EC_{50}$ of 45 µM.

Within the polyhydroxylated 1,4-naphthoquinone molecules produced by sea urchins, the equinoxin A is one of the most studied. Extracts from the sea urchins *Echinus esculentus* or *Tetrapygus niger*, enriched in EqA possess a broad antibacterial activity against Gram-positive and Gram-negative bacteria, which turns it into a molecule with a high biotechnological and pharmacological interest.

In some species of sea urchin, unfertilized eggs have a high content of equinochrome A and other polyhydroxylated 1,4-naphthoquinones, while in other species of sea urchins the eggs possess carotenoids instead of polyhydroxylated 1,4-naphthoquinones.

In *Tetrapygus niger*, the females can re-produce eggs one month after spawning, in a total reproductive period of 9 months (Zamora & Stotz, Chilean Journal of Natural History (1993) 66:155-169). We have demonstrated the presence of EqA and spinochromes, such as, for example, spinochromes B and E in the eggs of *T. niger* females and it is probable that these molecules play a protective role in the ova and the embryo. In ova of other sea urchin species this pigment is released into the extracellular medium during exposure to an acidic environment (Shapiro, Journal of General Physiology (1946) 29:267-275.).

The antioxidant activity of EqA has been used in medicine for the treatment of acute myocardial infarction, coronary diseases (U.S. Pat. No. 6,410,601), inflammatory diseases of the retina and cornea (U.S. Pat. No. 6,384,084) and treatment of amyloidosis (US20110065657). The use of EqA and other polyhydroxylated naphthoquinones was patented as colored antimicrobial agents as a supplement for food, textiles, hides and agricultural products (U.S. Pat. No. 6,159,585), or as a hair dye (U.S. Pat. No. 4,888,026 A).

The proposed applications for EqA and other polyhydroxylated 1,4-naphthoquinones suggest that these molecules are not cytotoxic and have broad pharmaceutical and industrial applications, for their antioxidant and antibiotic properties. Therefore, it is of great interest to obtain a new method for obtaining these polyhydroxylated 1,4-naphthoquinones under appropriate conditions for the pharmaceutical industry, ie without contaminants that could be toxic and of low environmental impact for marine resources.

Different methods for the production of EqA and spinochromes are described in the state of the art, however, all of them have in common an organic extraction of the echinochrome with toxic organic solvents and in the presence of acids such as hydrochloric acid or sulfuric acid, using as raw material the spines and shells of the urchins.

The present invention describes a new methodology for obtaining from sea urchin eggs an extract enriched in 6-ethyl-2,3,5,7,8-pentahydroxy-1,4-naphthoquinone (echinochrome A) and other polyhydroxylated 1,4-naphthoquinones, such as 2,3,5,7-tetrahydroxy-1,4-naphthoquinone (spinochrome B), 2-acetyl-3,5,6,7,8-pentahydroxy-1,4-naphthoquinone (spinochrome C), 2,3,5,6,8-pentahydroxy-1,4-naphthoquinone (spinochrome D) and 2,3,5,6,7,8-hexahydroxy-1,4-naphthoquinone (spinochrome E). The method of the invention comprises chemically inducing the spawning of female sea urchins and extracting the 1,4-naphthoquinones from the eggs, using non-toxic organic solvents and in the absence of acids.

Among the known methods for producing polyhydroxylated 1,4-naphthoquinones from urchins are:

Patent RU 2283298 C1 (Sep. 10, 2006), which describes a method for producing EqA from fresh or thawed sea urchins, comprising washing the shells and spines with water to mechanically remove impurities, removing fats with hexane or chloroform and finally an extraction with an organic solvent containing an inorganic acid. The resulting extract is purified by extraction with chloroform and sublimation under vacuum at 220° C.

Patent RU 2305548 C1 (Sep. 10, 2007), which protects a method for obtaining the EqA from sea urchin shells with a treatment with an aqueous alkaline solution and then a treatment with an alcoholic solution (10%) with sulfuric acid (30%).

Patent RU 1508535 A1 (Aug. 27, 1996), which discloses a method for extracting the red pigment from the sea urchin using a dilute solution of sulfuric acid in ethanol, followed by an extraction with water/chloroform in a ratio of 1:1 v/v. The extract obtained is concentrated with a mixture of 1,4-dioxane/hexane in a ratio of 5:1 v/v. The resulting product is washed with hexane and dried in vacuo. The yield of the desired product is 0.05-0.06% by dry weight of raw material.

The publication of Mathieson & Thomson (Journal of the Chemical Society C, 153-160, 1971) discloses a method of production of EqA comprising the treatment of the raw material with hydrochloric acid, the extraction of the desired product from the sea urchins with ether, separating it into water-soluble sodium derivatives, purification by silica gel chromatography, and recrystallization. The yield of the product is 0.01% by dry weight of raw material.

Patent RU 2086145 C1 (Aug. 10, 1997) describes a methodology for the production of a food additive enriched in EqA from sea urchin, which consists of processing with hydrochloric acid 2-12% at pH 5.0-5.2, washing, drying and grinding of the product.

Patent RU 2432956 (Nov. 10, 2011) discloses a method that divides the sea urchin into 4 parts: ova, ovarian fluid, viscera and shell. The eggs are used to recover ganglioside and phospholipid molecules (not Eq A, nor other polyhydroxylated 1,4-naphthoquinones); while shells and spines are used to extract pigments with oxalic acid or with chloroform and diethyl ether.

All these methods of EqA extraction have as a great disadvantage the use of large volumes of toxic organic solvents, either acids or concentrated bases, which are inconvenient for food and pharmaceutical applications. These methodologies require additional processes to eliminate alkaline and acid residues, and solutions containing fat. Therefore, these technologies are of a high economic cost. In addition, these methods have an environmental impact and the need to establish measures to repopulate the marine resource. However, this does not occur with the proposed invention, since the sea urchin is kept alive and can be returned to its natural environment.

Another known method for specifically producing the polyhydroxylated 1,4-naphthoquinone EqA is by chemical synthesis. This technology includes reactive intermediary compounds with toxic characteristics, which can co-purify with the final product (Pokhilo et al., Chemistry of Natural Compounds (2008) 44: 287-291). In this way, chemical synthesis increases costs by needing to eliminate the intermediaries, which is one of the reasons why food industries and pharmaceutical industries prefer molecules of natural origin to the same molecules produced by chemical synthesis.

The new technology protected in this invention to obtain an extract enriched in polyhydroxy 1,4-naphthoquinones from sea urchin eggs, reduces the generation of toxic products and dispenses with the use of acids and bases. Additionally, by keeping the urchins alive, it makes it an ecologically sustainable method.

This methodology is novel and differs from other known methods for producing EqA or other polyhydroxylated 1,4-naphthoquinones. The main advantages of the invention over the known methods are:

i) The natural source is sea urchin eggs enriched in these pigments (e.g., black urchin *Tetrapygus niger* eggs) and released by chemical induction, ii) the extraction process does not use acids such as hydrochloric acid or sulfuric acid nor bases, and iii) spawning by chemical induction and careful handling allows the urchins to be kept alive, reducing costs and environmental impact. Live urchins can produce new eggs after 1 month.

DESCRIPTION OF THE INVENTION

Figure 1:
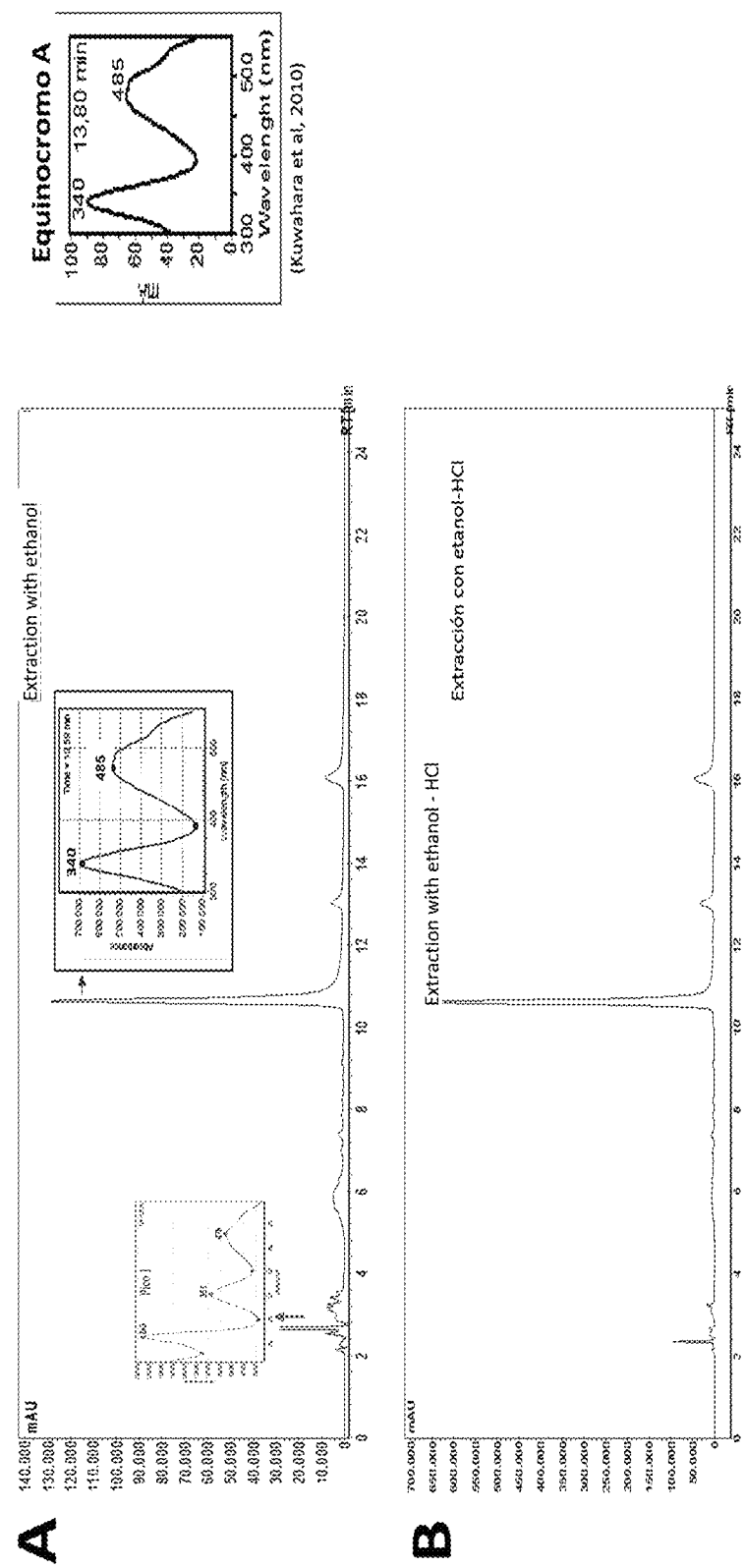
FIG. 1. HPLC chromatography of the organic extract obtained from sea urchin eggs (*Tetrapygus niger*), using extraction with ethanol (A) or ethanol and hydrochloric acid (pH 2) (B). The presence of EqA was monitored at 520 nm. The mobile phase is isocratic with formic acid 0.1% (50%), acetonitrile (32%) and methanol (18%) and a constant flow of 0.5 ml/min was used. The insert in the figure illustrates the absorbance spectrum of the main compound, which is similar to that reported by Kuwahara et al. (2010).

The invention relates to a new method for obtaining high purity polyhydroxylated 1,4-naphthoquinones, so that it can be used directly in the pharmaceutical and food industries.

A first innovation of the method of the invention with respect to what is known in the state of the art is the raw material used to obtain the polyhydroxylated 1,4-naphthoquinones. Currently, polyhydroxylated 1,4-naphthoquinones such as EqA are extracted mainly from the shells and spines of urchins. The invention proposes to obtain the polyhydroxy 1,4-naphthoquinones from urchin eggs, the first step of the method being then to chemically induce spawning. Since the raw material is ova and not shells or spines, the chemical conditions necessary for the extraction and purification of the EqA pigment are much milder, resulting in a lower expense and contamination associated with the process, given that acids or strong bases are not used.

In addition, the manipulation to induce the spawning process of the sea urchin eggs, which is used in this invention, allows the urchins to remain alive, which enables the production of more eggs by these urchins. In this way the procedure is renewable and sustainable.

Once the eggs are obtained, the process for obtaining the extract enriched in polyhydroxylated 1,4-naphthoquinones comprises the following additional steps: grinding the eggs until a fine powder is obtained, an extraction process with an alcoholic solvent, such as ethanol or methanol in absence of acids or bases, optionally a separation and/or concentration of the alcoholic extract and, if necessary, a final purification by liquid chromatography with a reversed phase column. If all these steps are carried out, the yield of the product EqA is ~0.2% by dry weight of raw material, with a purity of ~98%.

In general terms, the invention relates to a method for obtaining polyhydroxylated 1,4-naphthoquinones from live sea urchins, comprising the following steps:
 a) injecting a saline solution into the perivisceral coelom of female sea urchins to induce spawning;
 b) collecting the eggs, and grinding them to obtain a fine powder;
 c) mixing said fine powder with an alcoholic solvent;
 d) separating the alcohol supernatant comprising the polyhydroxylated 1,4-naphthoquinones in solution.

Optionally comprising concentrating, separating and/or purifying from the alcoholic supernatant obtained in step d) the polyhydroxylated 1,4-naphthoquinone molecules. In one embodiment the alcohol supernatant is precipitated using another organic solvent, or subjected to evaporation, for example under vacuum; and the crystals are resuspended in ethanol to obtain polyhydroxylated 1,4-naphthoquinones with high degree of purity. In one embodiment, the alcohol supernatant is concentrated by evaporation and purified by HPLC. In another embodiment, the alcohol supernatant is concentrated by evaporation in vacuo, the obtained crystals are resuspended in ethanol and purified by HPLC.

Where the KCl salt used in step a) is in a concentration range between 0.1 M to 2 M, and in a volume between 0.1 to 2 mL.

To grind the eggs, as indicated in step b) these are optionally frozen or dried. The alcohol solvent of step c) is preferably selected from methanol, ethanol or mixtures thereof.

The polyhydroxylated 1,4-naphthoquinones are purified equinochrome A (6-ethyl-2,3,5,7,8-pentahydroxy-1, 4-naphthoquinone), spinochrome A (2-acetyl-3,5,6,8-tetrahydroxy-1,4-naphthoquinone), spinochrome B (2,3,5,7-tetrahydroxy-1,4-naphthoquinone), spinochrome C (2-acetyl-3,5,6,7,8-pentahydroxy-1, 4-naphthoquinone), spinochrome D (2,3,5, 6,8-pentahydroxy-1, 4-naphthoquinone), spinochrome E (hexahydroxy-1,4-naphthoquinone) or mixtures thereof.

The process of the invention begins with spawning, which is induced by injection of KCl (0.5 M) into the perivisceral coelom. The induced urchin females are deposited on a smaller diameter vessel, which contains filtered and sterile seawater, where the eggs are received. The collected eggs are filtered, preferably using a fine sieve of pore size 1/32 inches (0.079375 centimeters) to remove impurities. Afterwards it is washed with filtered and sterile seawater. The excess water is subsequently removed by decanting the eggs. Then the eggs are dried at 60-80° C. for 24-72 hours, and are ground to a fine powder, which is cleaned by passing through a sieve of pore size 1/120 inches (0.021 centimeters). The product is then extracted by mixing the powder with methanol or ethanol at a proportion of 1:30 v/v under constant agitation. It is further filtered to remove the egg debris and evaporated under vacuum at 55° C. to 1/10 of the initial volume. The resulting extract is purified by chromatography with a C18 RP column, elution with 30-40% methanol to extract mainly spinochrome E, and finally an elution with 100% ethanol for the extraction of EqA. The resulting extract possesses equinochrome A with a purity of 99%. Finally the product is stored at −20° C. where it maintains a high stability for months.

The present invention in a preferred embodiment allows 6-ethyl-2,3,5,7,8-pentahydroxy-1,4-naphthoquinone (echinochrome A) to be obtained from sea urchin eggs, especially from black sea urchin (*Tetrapygus niger*) spawned by chemical induction, followed by extraction with ethanol or methanol without acids or bases. Given its antimicrobial and antioxidant properties, the obtained EqA can be used in aquaculture, fish processing, the food and medical industry, veterinary medicine and cosmetology. In addition, it can be applied on inert surfaces, to provide antimicrobial properties.

In order to test the antibiotic activity of these compounds, the inventors studied the antibacterial activity, measured as minimum inhibitory concentration (MIC), of the black sea urchin (*Tetrapygus niger*) extract enriched in equinochrome A (85% purity) and the purified EqA. (99% purity) against various pathogenic bacterial strains of clinical origin, whose results are shown in Table 1.

The results show that the extract, which comprises a mixture of polyhydroxylated 1,4-naphthoquinones, has better antibiotic activity than pure EqA, although both the extract and EqA show good results against strains resistant to conventional antibiotics.

TABLE 1

Antimicrobial activity of sea urchin extract *Tetrapygus niger* enriched in equinochrome A (85% purity) and EqA (99% purity) against various pathogenic strains

| Bacteria of clinical origin | Origin of the clinical isolate | Antibiotic resistance | MIC of EqA (µg/ml) pH 5 | pH 7 | MIC of Extract (µg/ml) pH 5 | pH 7 |
|---|---|---|---|---|---|---|
| GRAM POSITIVE | | | | | | |
| *S. aureus* | tracheal aspirate | penicillin | 8 | 32 | 4 | 16 |

TABLE 1-continued

Antimicrobial activity of sea urchin extract *Tetrapygus niger* enriched in equinochrome A (85% purity) and EqA (99% purity) against various pathogenic strains

| Bacteria of clinical origin | Origin of the clinical isolate | Antibiotic resistance | MIC of EqA (µg/ml) pH 5 | MIC of EqA (µg/ml) pH 7 | MIC of Extract (µg/ml) pH 5 | MIC of Extract (µg/ml) pH 7 |
|---|---|---|---|---|---|---|
| | hemocultivo | penicillin | 8 | 32 | 4 | 16 |
| | hemocultivo | penicillin | 8 | 32 | 4 | 16 |
| | hemocultivo | penicillin | 8 | 32 | 4 | 16 |
| | hemocultivo | penicillin, oxacillin, erythromycin, clindamycin, ciprofloxacin | 32 | 32 | 16 | 16 |
| GRAM NEGATIVA | | | | | | |
| *E. coli* | hemocultivo | ampicillin, chloramphenicol, cotrimoxazole | 32 | >64 | 16 | 64 |
| | hemocultivo | — | 32 | >64 | 16 | 64 |
| | urine | ampicillin, aztreonam, cefepime, cefotaxime, ceftazidime, ciprofloxacin | 32 | 64 | 16 | 32 |
| *Klebsiella oxytica* | hemocultivo | ampicillin | 64 | >64 | 16 | 32 |
| *Klebsiella pneumoniae* | urine | ampicillin, aztreonam, cephalothin, cefepime, cefotaxime, ceftazidime, ertapenem, nitrofurantoin | 64 | >64 | 16 | 32 |
| | urine | ampicillin, aztreonam, cephalothin, cefepime, cefotaxime, ceftazidime, nitrofurantoin | 64 | >64 | 16 | 32 |
| | hemocultivo | ampicillin, aztreonam, cephalothin, cefepime, cefotaxime, ceftazidime, ciprofloxacin, chloramphenicol, colistin, cotrimoxazole, gentamicin. | 64 | >64 | 16 | 32 |
| *Pseudomona aeruginosa* | hemocultivo | cefepime, ceftazidime, ciprofloxacin, gentamicin | 32 | >64 | 16 | 32 |
| | cateter | ampicillin, aztreonam, cefepime, ceftazidime, imipenem, meropenem | 32 | >64 | 16 | 32 |
| | aspirado traqueal | ampicillin, aztreonam, cefepime, ceftazidime, imipenem, meropenem | 32 | >64 | 16 | 32 |
| | aspirado traqueal | ampicillin, ciprofloxacin, imipenem, meropenem | 32 | >64 | 16 | 32 |
| | aspirado traqueal | ampicillin, aztreonam, ceftazidime, imipenem, meropenem | 64 | >64 | 16 | 32 |

MIC, minimum inhibitory concentration.

As we have indicated, the polyhydroxylated 1,4-naphthoquinones of sea urchin, such as EqA, possess a high antioxidant activity, which was demonstrated by the DPPH radical capture assay (2,2-diphenyl-1-picrylhydrazyl). The antioxidant activity of EqA, which was observed in the DPPH assay carried out by the authors of this invention, was greater than the antioxidant activities of α-tocopherol and ascorbic acid, both compounds recognized for their antioxidant activity. The antioxidant activity of EqA is dependent on the concentration of the pigment, the pH and the concentration of calcium. In the absence of calcium, the antioxidant activity is observed only at alkaline pH, but in the presence of calcium, the antioxidant activity is observed at alkaline pH and neutral pH, by the formation of stable semiquinone-calcium complexes (Levedeb et al., Archives of Biochemistry and Biophysics (2003) 413: 191-198). The invention is illustrated in the following examples:

EXAMPLE 1

In the present method, female sea urchins (black urchin *Tetrapygus niger*) are induced to spawn by injecting 0.1-1.0 ml of KCl (0.5 M) between the teeth and the hard outer shell. For the release of the red eggs, the urchin is placed face up on a precipitated glass or some other container of smaller diameter than the urchin, which contains filtered and sterile seawater. The eggs collected at the bottom of the container are washed of solid impurities with filtered and sterile seawater, and by filtration through a metallic sieve of pore size 1/32 inch (0.079375 cm) until all the solid impurities have been removed. The eggs are decanted to remove excess water, prior to processing or storage at −20° C. The eggs are dried at 60-80° C., milled and filtered through a sieve of pore size 1/120 inch (0.021 cm). Fifty ml of eggs are poured onto 1500 ml of ethanol or methanol and incubated at room temperature under constant agitation for 24-48 hours. The extract is collected and the raw material is re-extracted in methanol until no more red color is observed.

The extracts are mixed, concentrated at 55° C. in vacuo to obtain $\frac{1}{10}$ of the initial volume. The purification is performed by HPLC with a C18 RP column, washed with 30%-40% methanol to elute spinochrome E or other pigments, and finally elute the EqA with 100% ethanol. The spectrum is shown in FIG. 1A.

EXAMPLE 2

108 grams (wet weight) of sea urchin eggs (black urchin *Tetrapygus niger*) are extracted and incubated with 3 liters of methanol. 6 extractions are made until the extract shows no red color. The extracts are concentrated with a rotary evaporator to a volume of 150 ml. Water is added to a final volume of 400 ml and then chromatography of the extract is carried out by a C18 column, previously calibrated with water. Elutions are performed with 10% methanol, 30% methanol and 40% methanol, eluting spinochrome E or other pigments with a lower degree of hydrophobicity than EqA. Then, the EqA retained in the column is eluted with ethanol or methanol (100%), presenting a high purity (>90%).

EXAMPLE 3

Fifty ml of fresh or frozen and washed eggs are poured onto 1500 ml of methanol, and then processed and extracted as described in Example 1.

EXAMPLE 4

The product obtained from Example 1 or Example 3 is precipitated using another organic solvent, or subjected to evaporation. Finally the crystals are resuspended in ethanol to obtain equinochrome A with a high purity (>99%).

The concentration of EqA in ethanol was quantified at 341 nm, considering its molar extinction coefficient of 10650 ($M^{-1} \times cm^{-1}$). The samples were diluted to readings between 0.2 and 1.0 absorbance units. The readings were made in triplicate. The purity of the product was determined by high performance liquid chromatography (HPLC) with diode array detector (DAD). A C18 RP column (250 mm×4.6 mm, 3.5 µm) was used. La presencia de EqA se monitoreó a una longitud de onda de 520 nm. Se utilizó un flujo de 0.5 mL/min, con una temperatura de horno de 25° C. The presence of EqA was monitored at a wavelength of 520 nm. A flow of 0.5 mL/min was used, with an oven temperature of 25° C. The mobile phase consisted of a mixture of 50% formic acid 0.1% (solution A), 32% acetonitrile (solution B) and 18% methanol (solution C). Under these conditions the EqA had a retention time of 10.6 minutes. This product was identified by its absorbance spectrum with 2 absorption maximums at 341 and 468 nm, as described by Kuwahara et al. (2010). Alternatively, at a constant flow of 0.5 ml/min the following gradient was used: 0-3 min, solution A (95%), solution C (5%); 3-7 min, solution A (75%), solution B (10%), solution C (15%); 7-15 min solution B (30%), solution C (70%); 15-18 min, solution C (100%); 20 min, solution A (95%), solution C (5%). Under these conditions the EqA had a retention time of 14.8 min.

Figure 2:
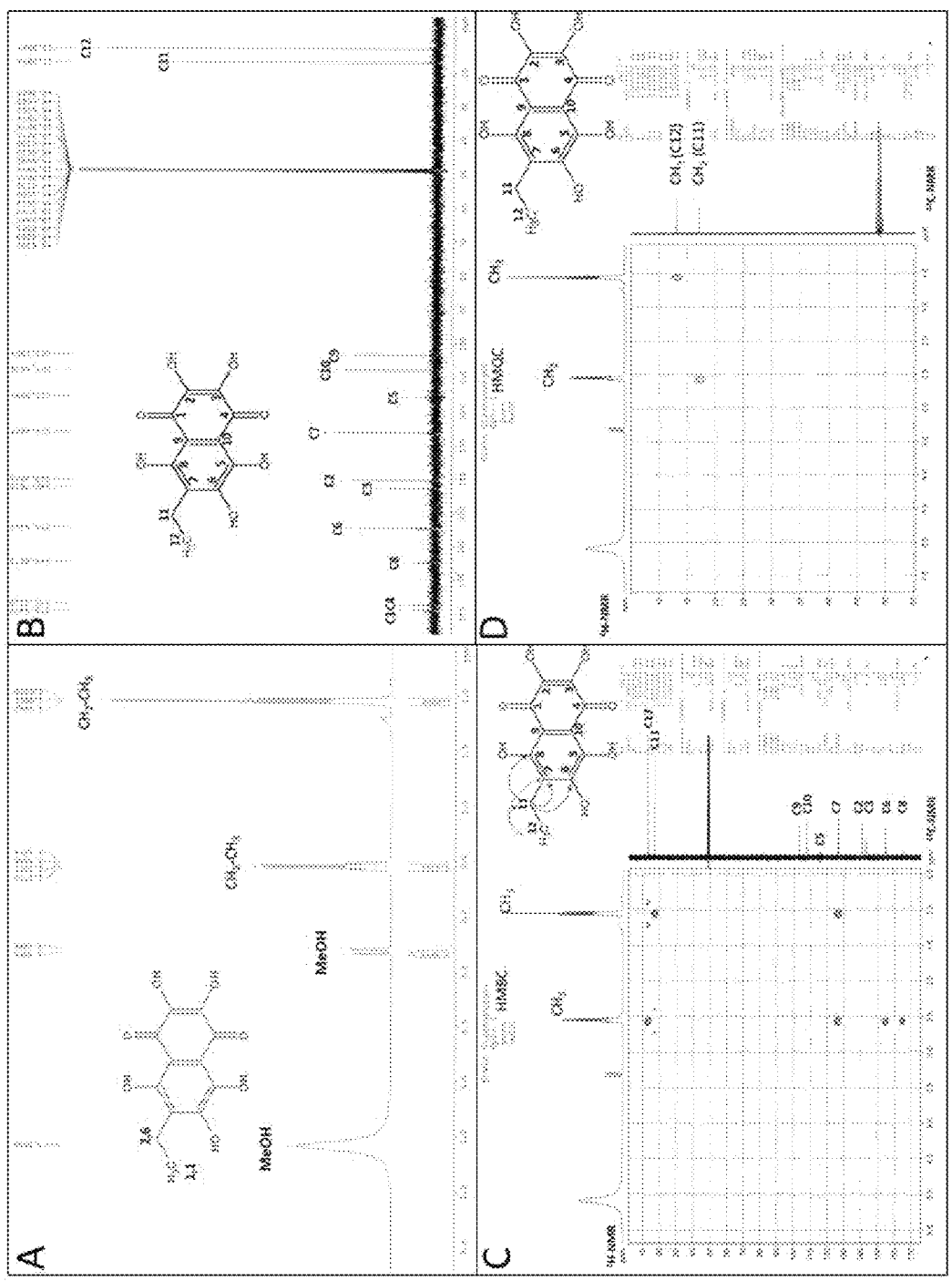
FIG. 2. Nuclear Magnetic Resonance Analysis of the main compound present in the organic extract of sea urchin (*Tetrapygus niger*). $H^1$ NMR (A), $C^{13}$ NMR (B), two-dimensional heteronuclear NMR HMBC (Acronym in English: Heteronuclear Multiple Bond Correlation) and HMQC (Acronym in English: Heteronuclear Multiple Quantum Correlation). The analysis that correlates the NMR signals with the 6-ethyl-2,3,5,7,8-pentahydroxy-1,4-naphthoquinone structure (equinochrome A) is included.

The mass of the purified EqA was determined by MALDI-TOF by analyzing the positive ion having a mass m/z 267 [M–H+], deducting a mass of 266 u.m.a. This value corresponds to that reported by Kuwahara et al. (2010). Nuclear magnetic resonance analysis of protons, carbon 13, and two-dimensional analysis of heteronuclear correlation HMBC (Acronym in English: Heteronuclear Multiple Bond Correlation) and HMQC (Acronym in English: Heteronuclear Multiple Quantum Correlation) confirm the structure of Echinochrome A as 6-ethyl-2,3,5,7,8-pentahydroxy-1,4-naphthoquinone (FIG. 2).

In the extract which contains EqA (85-90%) and another compound (10%) that has a retention time of 6 min in the HPLC chromatogram (FIG. 1A). This compound has an absorbance spectrum with two maximums at 353 nm and 478 nm, which correspond to the values reported for spinochrome E (hexahydroxy-1-4-naphthoquinone). The mass spectrometric analysis by MALDI-TOF of this compound indicates a positive ion of mass m/z 255 [M–H+], which allows the deduction of a mass of 254 a.m.u., which corresponds to the molecular mass of spinochrome E. Consequently, it is concluded that the extract of sea urchin eggs of the invention contains spinochrome E.

The black sea urchin ova extract (*Tetrapygus niger*) possesses antimicrobial activity against various pathogenic bacterial strains, including some multiresistant strains of antibiotics, with a minimum inhibitory concentration in a range of 4-64 µg/ml (Table 1), where the maximum activity is at acidic pH. The purified EqA of this extract containing EqA (85%) possesses an antibiotic activity with a minimum inhibitory concentration between 8 and 64 µg/ml (Table 1) on pathogenic bacteria which are multiresistant to antibiotics. This result suggests that the antibiotic activity of the extract is mainly due to the presence of EqA.

The antioxidant activity of the purified extract and equinochrome A was evaluated by the DPPH radical capture assay (2, 2-diphenyl-1-picryihydracil) (Shankarlal et al., (2011) Am-Euras, J. Sci. Res. 6:178-181). The EC50 of equinochrome A extract (85% EqA) for this assay was 18 µM and the EC50 of pure equinochrome A (99% purity) was 13 µM. Under these conditions the $EC_{50}$ of α-tocoferol is 100 µM and of ascorbic acid is 45 µM, indicating a higher antioxidant activity of pure EqA against these known antioxidants. These results also suggest that the EqA possesses the main antioxidant activity of the extract of the invention.

EXAMPLE 5

In order to compare the method of the invention with respect to the traditional method, an extraction was made from the eggs adjusting the pH to 2 with hydrochloric acid.

For which HCl was added to 50 ml of eggs until it reached a pH of 2, later the acidified eggs are poured on 1500 ml of ethanol or methanol and incubated at room temperature in constant agitation for 24-48 hours. The extract is collected and the raw material is re-extracted in methanol until no more red color is observed.

The extracts are mixed, concentrated at 55° C. in vacuo to obtain $\frac{1}{10}$ of the initial volume. The purification is performed by HPLC with a C18 RP column, washed with 30%-40% methanol to elute spinochrome E or other pigments, and finally elute the EqA with 100% ethanol. The spectrum of this comparative example is shown in FIG. 1B.

The extraction with ethanol and hydrochloric acid and the extraction with ethanol without hydrochloric acid, make it possible to obtain the same final product (FIGS. 1A and 1B), which corresponds to equinochrome A. The absorbance spectrum and the mass spectrum of the product correspond to the absorbance and mass spectra of EqA (Kuwahara et al., LWT-Food Science and Technology (2010) 43:1185-1190). This is expected since in the traditional method hydrochloric acid is used to dissolve the calcareous structure of shells and spines of urchin, which are the raw material of said traditional method. However, because the eggs of urchins do not have a calcareous structure, when comparing extraction with HCl, or traditional, with the method of the invention, we verify that there are no differences in the profile of molecules eluted with both methods.

In this way, the invention makes it possible to obtain polyhydroxylated 1,4-naphthoquinones without residues of hydrochloric acid, or of any other strong acid or base, since it is not used in its extraction.

The invention claimed is:

1. A method for obtaining polyhydroxy 1,4-naphthoquinones from live sea urchins comprising:
   a) injecting a potassium chloride saline solution into the perivisceral coeloma of female sea urchins to induce spawning which produces eggs;
   b) collecting the eggs, and grinding them into a fine powder;
   c) mixing said fine powder with ethanol or methanol to form an ethanol or methanol supernatant;
   d) separating out the ethanol or methanol supernatant which comprises the polyhydroxy 1,4-naphthoquinones in solution,
   wherein the potassium chloride is used at a concentration range between 0.1 M to 2 M and in a volume of solution between 0.1 ml to 2 ml, the method is performed in the absence of acid and base and wherein the sea urchins are kept alive.

2. The method of claim 1, wherein the polyhydroxy 1,4-naphthoquinones are concentrated, separated or purified from the ethanolic or methanolic supernatant obtained in step d).

3. The method of claim 2, wherein the ethanolic or methanolic supernatant is precipitated using a different organic solvent or subjected to evaporation wherein the resulting crystals are resuspended in ethanol to obtain polyhydroxylated 1,4-naphthoquinones with a high degree of purity.

4. The method of claim 2, wherein the methanolic or ethanolic supernatant is concentrated by evaporation and purified by High performance liquid chromatography.

5. The method of claim 1, wherein the polyhydroxy 1,4-naphthoquinones are selected from the group consisting of echinochrome A (6-ethyl-2,3,5,7,8-pentahydroxy-1,4-naphthoquinone), spinochrome A (2-acetyl-3,5,6,8-tetrahydroxy-1, 4-naphthoquinone), spinochrome B (2,3,5,7-tetrahydroxy-1,4-naphthoquinone), spinochrome C (2-acetyl-3, 5,6,7,8-pentahydroxy -1,4-naphthoquinone), spinochrome D (2,3,5,6,8-pentahydroxy-1,4-naphthoquinone), spinochrome E (hexahydroxy-1,4-naphthoquinone) and mixtures thereof.

* * * * *